US011622548B2

(12) United States Patent
Urbanski et al.

(10) Patent No.: US 11,622,548 B2
(45) Date of Patent: Apr. 11, 2023

(54) APPARATUS AND METHOD FOR REARING OR BREEDING OF INSECTS (71) Applicant: HIPROMINE S.A., Robakowo (PL)

(72) Inventors: Jakub Urbanski, Warsaw (PL); Damian Józefiak, Poznan (PL); Jan Mazurkiewicz, Sady (PL)

(73) Assignee: HIPROMINE S.A., Robakowo (PL)

( * ) Notice: Subject to any disclaimer, the term of this patent is extended or adjusted under 35 U.S.C. 154(b) by 36 days.

(21) Appl. No.: 16/324,325

(22) PCT Filed: Aug. 7, 2017

(86) PCT No.: PCT/IB2017/054828
§ 371 (c)(1),
(2) Date: Feb. 8, 2019

(87) PCT Pub. No.: WO2018/029597
PCT Pub. Date: Feb. 15, 2018

(65) Prior Publication Data
US 2019/0166812 A1 Jun. 6, 2019

(30) Foreign Application Priority Data

Aug. 9, 2016 (PL) .......................................... 418244

(51) Int. Cl.
*A01K 67/033* (2006.01)
(52) U.S. Cl.
CPC .................................. *A01K 67/033* (2013.01)
(58) Field of Classification Search
CPC .... A01K 67/033; A01K 1/032; A01K 31/005; A01K 67/00; A01K 67/02; A01K 67/0332
See application file for complete search history.

(56) References Cited

U.S. PATENT DOCUMENTS 3,941,089 A * 3/1976 Andreev .............. A01K 67/033
119/6.6
4,148,276 A * 4/1979 Schmidt ................ A01K 31/04
119/439
(Continued)

FOREIGN PATENT DOCUMENTS

CN       203748476 U     8/2014
CN       104221797 A    12/2014
(Continued)

OTHER PUBLICATIONS

KR-100556207-B1 machine translation (Year: 2006).*
JP200211440A Machine translation (Year: 2202).*

*Primary Examiner* — Son T Nguyen
(74) *Attorney, Agent, or Firm* — Dinsmore & Shohl LLP (57) ABSTRACT

A technological line for rearing and/or breeding of flightless insects and/or larval forms of insects includes at least one level, being an autonomous conveyor belt with lateral sidewalls on both sides. The sidewalls have upper edges curved inwardly at least once, with a bending angle not less than 30°. Transverse brackets extend generally perpendicularly to and connect the sidewalls, and support the belt. The sidewalls are structural elements supporting edges of the belt, so that both the conveyor belt and the lateral sidewalls form a trough profile, and the pressure of the mass of the insects, which are on the surface of the belt and potentially additionally of the feed and/or excrement of insects press down on the edges of the belt against the sidewalls. The brackets and the sidewalls are made of a material with efficient heat conducting properties. A modular system and a method utilize the technological line.

21 Claims, 6 Drawing Sheets

(56) References Cited

U.S. PATENT DOCUMENTS

| | | | | |
|---|---|---|---|---|
| 4,195,592 A | * | 4/1980 | Siciliano | A01K 31/005 |
| | | | | 119/456 |
| 4,262,633 A | * | 4/1981 | Taboga | A01K 67/0332 |
| | | | | 119/6.7 |
| 4,437,433 A | * | 3/1984 | Nijhof | A01K 31/007 |
| | | | | 119/455 |
| 4,480,588 A | * | 11/1984 | Holladay | A01K 31/005 |
| | | | | 119/455 |
| 5,570,657 A | * | 11/1996 | Kuhlmann | A01K 31/007 |
| | | | | 119/458 |
| 2002/0038757 A1 | * | 4/2002 | Eberle | B65G 15/08 |
| | | | | 198/820 |
| 2010/0129273 A1 | * | 5/2010 | Milin | C05F 17/05 |
| | | | | 422/187 |
| 2013/0319334 A1 | | 12/2013 | Newton et al. | |
| 2014/0123902 A1 | * | 5/2014 | Kitazumi | C05F 3/06 |
| | | | | 119/6.5 |
| 2014/0261188 A1 | * | 9/2014 | Chin | A01K 67/033 |
| | | | | 119/6.6 |
| 2020/0296939 A1 | * | 9/2020 | Rudolph | A01K 31/007 |

FOREIGN PATENT DOCUMENTS

| | | | |
|---|---|---|---|
| CN | 105075992 A | | 11/2015 |
| CN | 105432463 A | | 3/2016 |
| EP | 2703372 A1 | | 3/2014 |
| JP | 200211440 A | * | 1/2002 |
| KR | 100556207 B1 | * | 2/2006 |
| KR | 20120097205 A | | 9/2012 |
| WO | 2008040033 A2 | | 4/2008 |

* cited by examiner

Fig. 6b ional stage application of PCT/IB2017/054828, filed Aug. 7, 2017, which claims priority to PL P.418244, filed Aug. 9, 2016, the entire content of both of which is incorporated herein by reference.
APPARATUS AND METHOD FOR REARING OR BREEDING OF INSECTS

REFERENCE TO RELATED APPLICATIONS

This application is a U.S. national stage application of PCT/IB2017/054828, filed Aug. 7, 2017, which claims priority to PL P.418244, filed Aug. 9, 2016, the entire content of both of which is incorporated herein by reference.

FIELD OF THE INVENTION

The object of the invention is a technological line for rearing and/or breeding of flightless insects and/or larval forms of insects. The invention also relates to a modular system of technological lines for rearing and/or breeding of flightless insects and/or larval forms of insects, a method of rearing and/or breeding of flightless insects and/or larval forms of insects and use of the technological line and the modular system of the invention for rearing and/or breeding of flightless insects and/or larval forms of insects.

BACKGROUND OF THE INVENTION

In recent years the industrial breeding of insects has been indicated as a sustainable alternative to protein and fat production for feed uses, including farm animal feeding and food purposes (Food and Agriculture Organization of the United Nations 2012 Assessing the potential of insects as food and feed in assuring food security. Summary report. Technical consultation meeting 23-25 January, FAO, Rome, Italy).

The review publication Makkar H. P. S., Tran G., Heuze V., Ankers P. (2014) State-of-the-art on use of insects as animal feed. Animal Feed Science and Technology, 197, 1-33, presents the results having been accomplished so far in the world of attempts to use different species of insects for animal feeding, referring to unexploited potential of this group of organisms being a raw material for direct feeding or processing into high quality protein components.

Currently used technologies of insects breeding and rearing are based on rack systems or self-supporting systems using small size containers for rearing insects. It is standard to use plastic containers or boxes for breeding. This solution hinders automating feed distribution (lack of direct access to each container) and emptying the containers with reared insects and their separation from the substrate and excrements cumulating at the bottom.

At the same time, due to small size containers, generally below 0.5 m$^2$, gaseous exchange and dissipation of moisture and excess metabolic heat are hindered, reducing the permissible quantity of insects per unit area because of the risk of overheating.

The continuous feeding of insects, relevant for intensive breeding, can lead to overheating of insects, condensation of metabolic water and finally to poisoning with metabolites. At the same time, both the layout of the containers for breeding and the limited maximum density of insects per unit area make the usage of the feed in liquid or semi-liquid form difficult or impossible.

In the case of currently used breeding containers another problem arises with maintaining an appropriate level of bio-assurance and effective protection against uncontrolled escape of the insects. Actions meant to raise the level of bio-assurance such as securing the openings in the containers with mesh or coatings make functionality of the containers limited and increase significantly the amount of labor input and time needed to handle the breeding, thereby raising the cost of insects production.

The object of present invention is to overcome the above-mentioned disadvantages of the state of the art. This object has been achieved by developing a technological solution which enables partial or total automation of rearing processes and reduction of breeding units needed for producing a determined weight of insects, while making it possible at the same time to optimize the use of livestock buildings.

The present inventors have unexpectedly found that it is preferable to use a technological line, for example a multi-level system, where at least one level, preferably each one, is an autonomous conveyor belt with sidewalls, preferably including a carrier system enabling installation of automatic feeders. The conveyor belt allows to clear a level after a rearing cycle has been completed. The sidewalls and brackets structure allows efficient water and metabolic heat removal, protecting the insects effectively against overheating and increasing allowed density of insects per unit area. The present inventors have found that using self-sealing sidewalls allows raising the level of bio-assurance.

SUMMARY OF THE INVENTION

Studies carried out by the inventors have shown that using conveyor belts with profiled sidewalls significantly increases efficiency of rearing insect larvae, while at the same time raising the degree of automation of the accompanying processes of rearing. The system also allows recovering metabolic heat of the insects and the employed shape of the sidewalls allows raising the level of bio-assurance.

The object of an invention is a technological line for rearing and/or breeding of flightless insects and/or larval forms of insects, having at least one level, the level being an autonomous conveyor belt with lateral sidewalls placed on both sides along the direction of the conveyor belt's movement having upper edges bent inwardly at least once, the bending angle of the edge of each sidewall being not less than 30°, preferably comprised between 30° and 90° and transverse brackets, extending generally perpendicularly to the lateral sidewalls, supporting the belt of the conveyor, connecting the opposite profiled lateral sidewalls, wherein the profiled lateral sidewalls are also structural elements supporting longitudinal edges of the belt of the conveyor, so that both the conveyor belt and the lateral sidewalls form a trough profile; and the pressure of the mass of the insects, being on the surface of the conveyor belt and potentially additionally of the feed and/or excrements of the insects causes pressing down of the longitudinal edges of the conveyor belt against the profiled lateral sidewalls; whereas both the transverse brackets and the profiled lateral sidewalls are made of a material with efficient heat conducting properties.

In a preferred embodiment of the technological line, according to the invention, each lateral sidewall has an additional longitudinal bending line with the upper edge bent inwardly to the trough profile at least twice and the other bending angle of each sidewall is preferably not less than 90°.

In a preferred embodiment of the technological line, according to the invention, the height of the profiled lateral sidewalls is not less than twice the maximum length of a given insect.

Preferably, according to the invention, the technological line includes brackets connecting the opposite legs, whereas the brackets have no less than one hole which allows installation of automatic feeders.

Preferably, in accordance with the invention, the technological line includes an automatic system for supplying feed; preferably, a multi-point automatic system for supplying feed.

In a preferred embodiment of the technological line, in accordance with the invention, the automatic system for supplying feed allows to provide wet or semi-liquid feed with water content of 15-45%, preferably, subjected to natural or directional pre-fermentation.

Preferably, each conveyor belt is from 2 to 110 m long and from 0.5 to 3 m wide. In a preferred embodiment of the technological line the transverse brackets and/or the profiled lateral sidewalls are made of metal, preferably of stainless or galvanized steel.

Preferably one or more conveyor belts are made of plastic, preferably of polyvinyl chloride (PVC), polypropylene (PP), or polystyrene (PS). In a preferred embodiment of the technological line, in according to the invention, the spaces between levels are maintained as not less than the height of the profiled lateral sidewalls.

In a preferred embodiment of the technological line, in according to the invention, it is a mobile structure, preferably adapted to move on rails or wheels.

The object of the invention is also a modular system of technological lines for rearing and/or breeding of flightless insects and/or larval forms of insects, which includes unified central modules including technological lines according to the invention, while additionally including a rear module and a front module, both equipped with transverse sidewalls, a rear end sidewall and a front end sidewall respectively, preferably movable, preferably equipped with a clamping mechanism, preferably with a compression spring.

In a preferred embodiment of the modular system, the rear and front module are equipped with tension systems, drive shafts and pressure rollers respectively, allowing to move the belt of the conveyor using a mechanical or a manual drive.

The object of the invention is also a method of rearing and/or breeding of flightless insects and/or larval forms of insects, which includes a step of rearing and/or breeding of flightless insects and/or larval forms of insects using the technological line according to the invention or the modular system according to the invention.

In a preferred embodiment of the method of rearing and/or breeding of flightless insects and/or larval forms of insects, the larval form of insects shall be larvae of mealworm beetles and/or larvae of hymenoptera *hermetia*.

In a preferred embodiment of the method of rearing and/or breeding of flightless insects and/or larval forms of insects, the larvae are provided with feed comprising fruit and vegetable pulp and grain mill products.

In a preferred embodiment of the method of rearing and/or breeding of flightless insects and/or larval forms of insects, the carrier elements and the profiled lateral sidewalls of the technological line according to the invention or of the modular system according to the invention are made of metal, which enables the weight of insects per unit area within the technological line according to the invention or within the modular system according to the invention to exceed 10 kg/m$^2$.

The object of the invention is also use of the technological line according to the invention or of the modular system according to the invention for rearing and/or breeding of flightless insects and/or larval forms of insects.

In a preferred example of the use of the technological line according to the invention or of the modular system according to the invention for rearing and/or breeding of flightless insects and/or larval forms of insects, the insects are larvae of mealworm (*Tenebrio molitor*) and/or larvae of *Hermetia* (*Hermetia illucens*).

The present inventors have unexpectedly found that when the profiled lateral sidewalls and the system of brackets, supporting the belts of the conveyor and connecting the opposite profiled lateral sidewalls, are made of a material with efficient heat conducting properties, preferably of metal, they function as a heat sink dissipating the excess metabolic heat emitted by the insects. This solution protects the insects against overheating, helping to compensate for the thermal gradient. The system of dissipating heat allows increasing of the number of lines and makes the use of breeding space more efficient by increasing the density of insects per unit area, which is followed by an increase in the efficiency of the breeding process.

The present inventors have also unexpectedly found that in the preferred embodiment comprising the lateral sidewalls made of metal, in addition, even better protection against escape of the insects is achieved, as the insects are reluctant to enter any metal surfaces and they stay on the surface of the belt of the conveyor, avoiding climbing the lateral sidewalls.

In the present application "material with efficient heat conducting properties" is intended to mean a material of high heat conductivity, preferably metal or any metal alloy.

In an embodiment, the system shall be made from the carrier elements, i.e. legs and brackets, connecting opposite legs, and the transverse brackets connecting the opposite profiled lateral sidewalls made of steel, preferably stainless or galvanized steel, with the conveyor belts preferably made of plastic or of fabric made of plastic, preferably of polyvinyl chloride (PVC), polypropylene (PP), or polystyrene (PS). The conveyor belts are equipped with the profiled lateral sidewalls constituting at the same time structural elements, which support the edge of the belt of the conveyor, as a result of which, the conveyor belt together with the upwardly bent edges of the profiled lateral sidewalls form a trough. The present inventors have unexpectedly found that under the working load self-sealing of the belt of the conveyor occurs, which makes the escape of the insects impossible and raises the level of bio-assurance. The present inventors have concluded that the shape of the profiled lateral sidewalls and their profile, with the edge bent inwardly to the system, make the structure of the system more robust, stiffening the sidewall and providing it with increased durability against the pressing-down of the mass of the insects and the feed which are in the trough, raising at the same time the level of bio-assurance by not allowing the insects to get outside. Preferably the shape, the profile and the height of the profiled lateral sidewalls should be adapted to the size of the reared insects, while, preferably, the minimum height of the profiled lateral sidewalls is not less than twice the maximum length of a given insect.

In the most preferred embodiment the spaces between the levels are maintained at a height equal to or greater than the height of the profiled lateral sidewalls. The space provides access to the individual levels and facilitates gaseous exchange, preferably utilizing a system of recuperative ventilation in the room containing the breeding lines.

The present inventors have found that the load-bearing structure of the technological line can be integrated with feed supplying system, preferably a multi-point one, improving rearing/breeding efficiency by minimizing the distance the insects need to cover to reach the nearest feed source. Preferably the feed supplying system allows employing wet or semi-liquid feed with water content of 15-45% (preferably, subjected to natural or directional pre-fermentation).

The present inventors have found that the load-bearing structure of the line should allow movement of the multi-level line perpendicularly to the longitudinal axis of the line, preferably on rails or wheels. The mobility of the system allows more efficient utilization of the space in the production hall, where more than one line is installed, by reducing the space necessary to ensure the communication routes along the lines.

In a preferred embodiment the modular system of the technological lines, according to the invention, shall be based on unified modules, including one or more unified middle modules and front and rear modules, which together make it possible to build the line having various length, wherein the front and rear modules are equipped with transverse sidewalls, respectively a rear end sidewall and a front end sidewall, preferably movable ones, preferably equipped with a clamping mechanism provided with automatic and/or semi-automatic transmission units and tensioners. In an embodiment, eight-level system consists of six middle modules, each of 125 cm in length and 100 cm in width, and one front and one rear module.

In a preferred embodiment, the front and rear modules are preferably equipped with drive shafts allowing to move the belt of the conveyor, e.g. made of plastic (PVC), using a mechanical or manual drive.

The object of the invention is also a method of rearing and/or breeding of larvae of insects undergoing complete metamorphosis (Holometabolia), preferably larvae of mealworm beetles and/or larvae of hymenoptera *hermetia*, wherein the larvae are reared/bred and fattened on t conveyor belts using a feed containing fruit and vegetable pulp and grain mill products.

The present inventors have unexpectedly found that utilization of the system enables to increase significantly the efficiency of rearing/breeding and to reduce the time for rearing/breeding due to the possibility of feeding the larvae in a continuous mode. The present inventors have also found that the system improves gaseous exchange and allows doubling the number of reared larvae per unit area, as compared to standard solutions applied to larvae rearing.

DETAILED DESCRIPTION OF THE INVENTION

For a better understanding of the invention, it has been illustrated in more detail in the examples, which are not limiting the scope of the invention.

EXAMPLES

Example 1: Technological Line for Rearing/Breeding Insects

Figure 1:
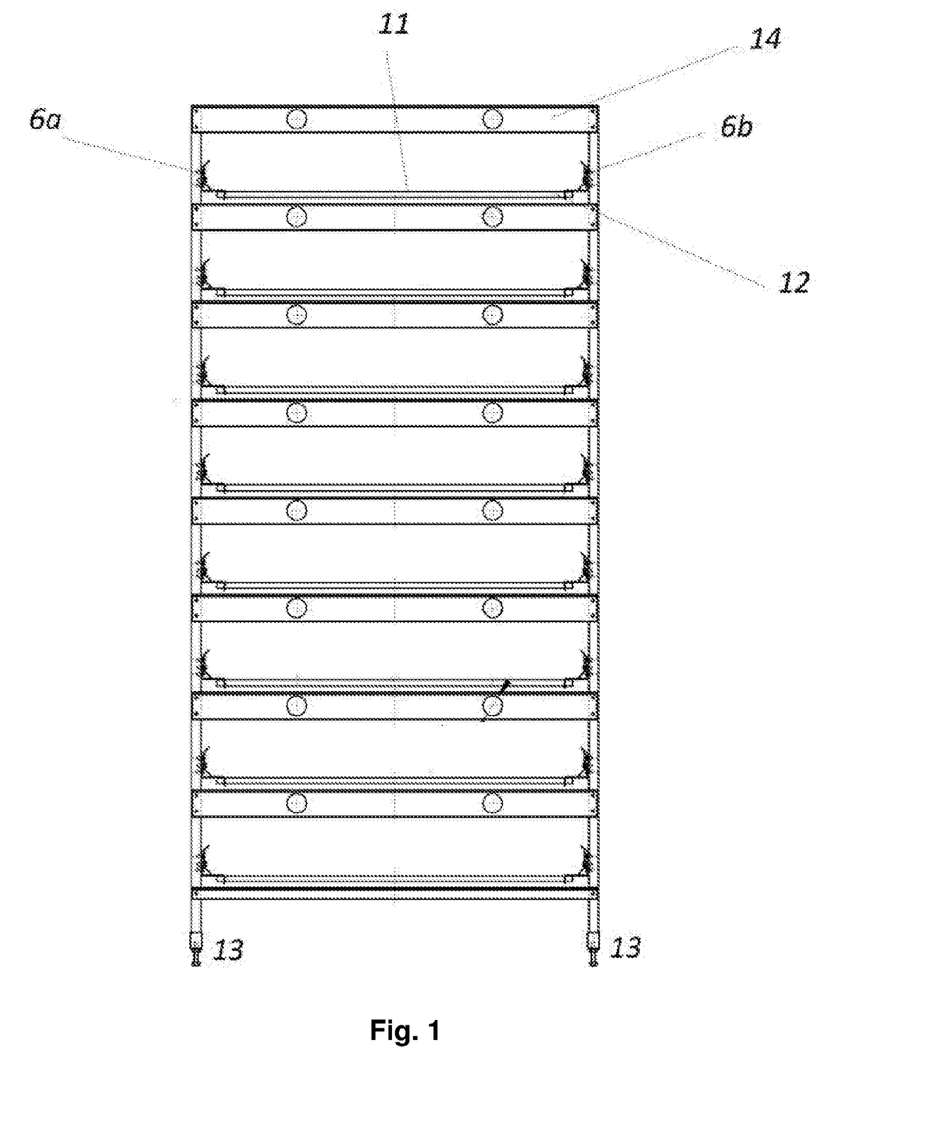
FIG. 1 shows a cross-section of an exemplary eight-level line.
Figure 2:
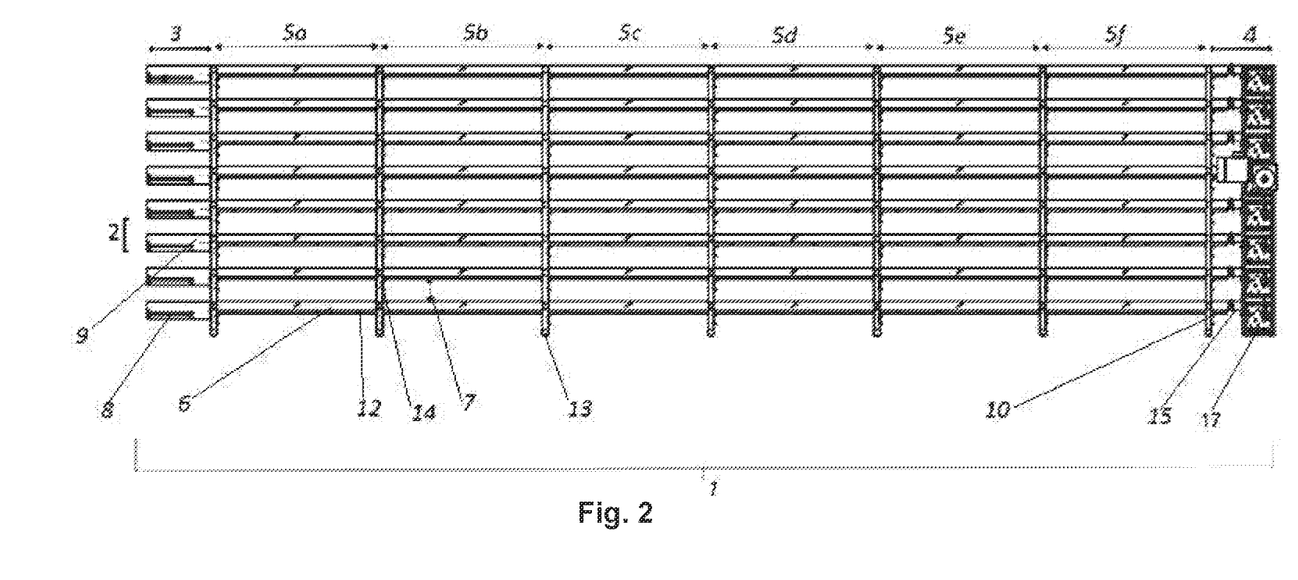
FIG. 2 shows a side view of an eight-level line made up of six middle modules 5a, 5b, 5c, 5d, 5e, 5f, a front module 4 and a rear module 3 for each level.

The technological line 1 for rearing and/or breeding of flightless insects and/or larval forms of insects, as shown at a cross-section in FIG. 1 and at a side view in FIG. 2, as a part of a modular system, includes at least one level 2, the level being an autonomous conveyor belt 11 with profiled lateral sidewalls 6a, 6b having upper edges curved inwards, with the profiled lateral sidewalls 6a, 6b being at the same time structural elements supporting the edges of the belt of the conveyor 11, so that both the conveyor belt 11 together with the upward curved edges of the profiled lateral sidewalls 6a, 6b form a trough profile.

FIG. 1 and FIG. 2 show the multi-level system of conveyor belts 11 including eight levels 2. Each conveyor belt 11 is 110 m long and 3 m wide, but these values of length and width may vary in other embodiments, preferably within the range between 2-110 m for length and 0.5-3 m for width, with the profiled lateral sidewalls 6a, 6b equipped with an autonomous carrier system, which includes legs 13 and brackets 14 connecting the opposite legs 13 and transverse brackets 12 connecting the opposite profiled lateral sidewalls 6a, 6b.

Figure 3:
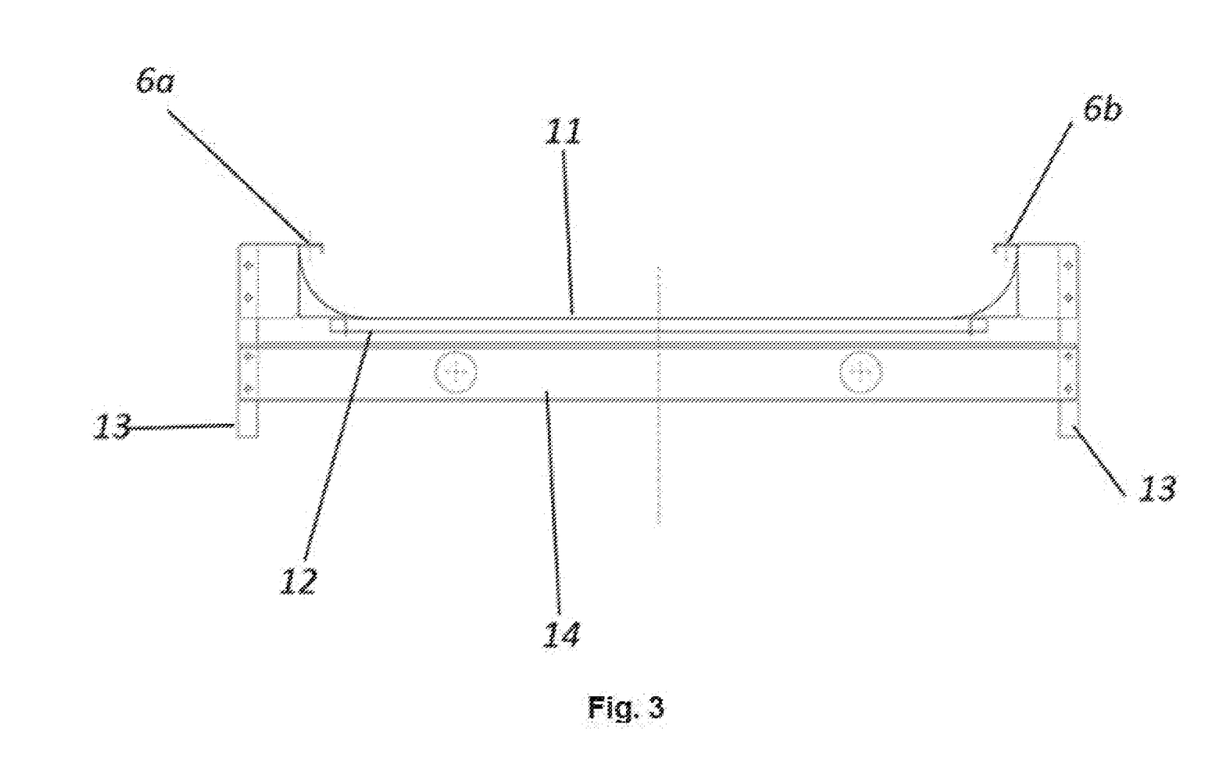
FIG. 3 shows a cross-section through one level for a preferred embodiment with a double-bend of the lateral sidewalls 6a, 6b, twice at an angle of $\alpha$, $\beta$ 90°.
Figure 6A:
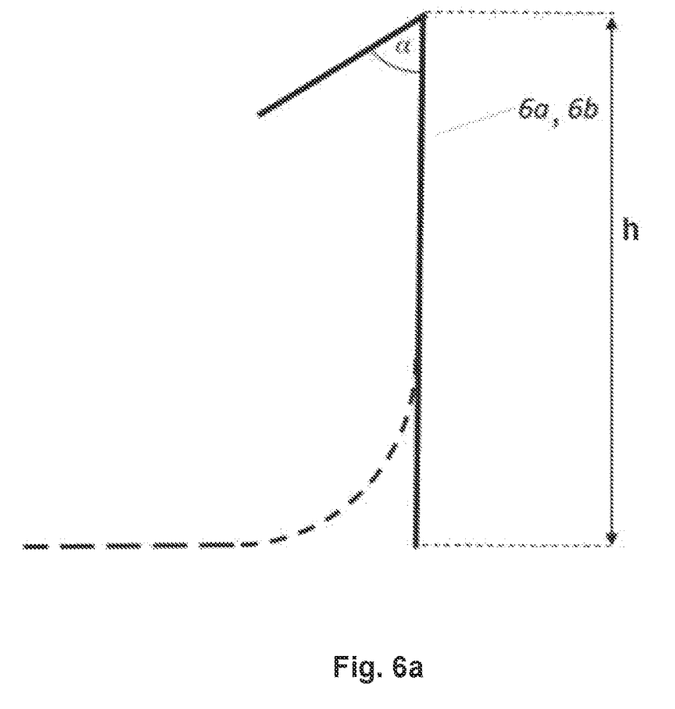
FIG. 6A shows in detail a lateral sidewall 6a, 6b bent once at an angle $\alpha$, at not less than 30°.
Figure 6B:
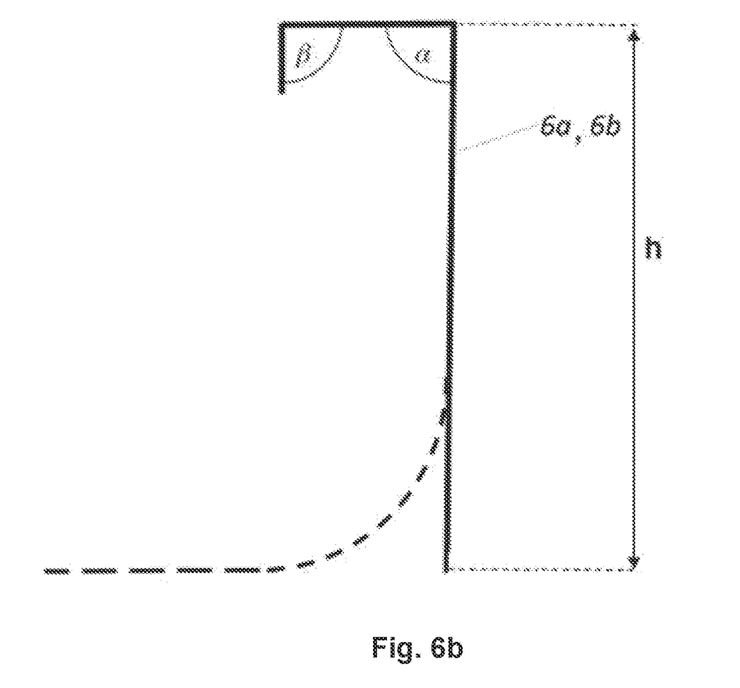
FIG. 6B shows in detail a lateral sidewall 6a, 6b bent twice at an angle $\alpha$, $\beta$ 90°, in according to a preferred embodiment as shown in FIG. 3; h means height of a lateral side wall 6a, 6b.

In the embodiment, the technological line is made from steel carrier elements with the conveyor belts 11 made of plastic. The conveyor belts 11 are equipped with the profiled lateral sidewalls 6a, 6b, which at the same time constitute structural elements, supporting the edge of the belt of the conveyor 11, so that the conveyor belt 11 together with the upward curved edges of the profiled lateral sidewalls 6a, 6b form a trough, while pressing down the edges of the belt of the conveyor against the lateral sidewalls in areas, where the surfaces are in contact. Under the working load self-sealing of the belt of the conveyor 11 occurs through pressing the edge of the belt of the conveyor down against the lateral sidewalls in areas, where the surfaces are in contact, which makes the escape of the insects impossible and raises the level of bio-assurance. The shape of the profiled lateral sidewalls 6a, 6b and their profile with an edge bent inwardly to the system make the structure of the system more robust, stiffening the sidewall and at the same time raising the level of bio-assurance. In the embodiment the shape, the profile and the height h of the profiled lateral sidewalls 6a, 6b is adapted to the size of the reared insects, while the height h of the profiled lateral sidewalls is not less than twice the maximum length of an insect, and the bending angle $\alpha$ of the edge of each sidewall 6a, 6b is 30° inwards. The alternative embodiments show that the bending angle $\alpha$ of the edge of each sidewall can be greater, preferably between 30-90° inwards. The alternative embodiments involve the bending angle $\alpha$ of the edge of each sidewall as follows: 30, 40, 45, 50, 55, 60, 65, 70, 75, 80, 85, 90, 100, 110 or 120°. Each embodiment of the lateral sidewalls shows that the sidewalls fulfill their function of bio-assurance, protecting against escape of the insects. In the preferred embodiment (FIG. 3 and FIG. 6) the edges of the lateral sidewalls 6a, 6b are bent two times inwards at an angle $\alpha$ of 90° and at an angle $\beta$ of 90°, forming a preferred edge, which makes an uncontrolled escape of the insects impossible. In alternative embodiments the escape of the insects is prevented due to the lateral sidewalls having various combinations of bending angles of the edges, with the bending angle α of the edge of each sidewall being 30, 40, 45, 50, 55, 60, 65, 70, 75, 80, 85, 90, 100, 110 or 120° and the bending angle β of the edge of each sidewall being 30, 40, 45, 50, 55, 60, 65, 70, 75, 80, 85, 90, 100, 110 or 120°.

Since the profiled lateral sidewalls 6a, 6b are made of metal, together with the system of metal transverse brackets 12 supporting the belt of the conveyor 11 and connecting the opposite profiled lateral sidewalls 6a, 6b, they function as a heat sink dissipating the excess metabolic heat emitted by the insects. The solution protects the insects against overheating, helping to compensate for the thermal gradient. The system of dissipating heat allows increasing the number of lines and makes the use of breeding space more efficient by increasing the density of insects per unit area.

Between the levels 2 spaces 7 are maintained with height equal to or greater than the height of the profiled lateral sidewalls 6a, 6b. The space 7 provides access to the individual levels 2 and facilitates gaseous exchange, optionally when utilizing a system of recuperative ventilation in the room containing the breeding lines.

The carrier structure of the technological line 1 can be integrated with a feed supplying system, also a multi-point one, improving rearing efficiency by minimizing the distance the insects need to cover to reach the nearest feed source. The feed supplying system may allow using wet or semi-liquid feed with water content of 15-45% (optionally, subjected to pre-fermentation).

The carrier structure of the line 1 allows movement of the multi-level line perpendicularly to the longitudinal axis of the line 1, for example on rails or wheels. The mobility of the system allows utilizing the space of the production hall more efficiently, where more than one line is installed, by reducing the space necessary to ensure the communication routes along the lines 1.

In the embodiment, the modular system of the technological lines is shown, which is based on unified modules, as shown in FIG. 2, allowing building the lines of various length, including middle modules 5a, 5b, 5c, 5d, 5e, 5f, wherein the rear module 3 and front module 4 are equipped with transverse sidewalls, the rear end sidewall 9 and the front end sidewall 10, being movable, equipped with a clamping mechanism, for example a pressure spring. In the embodiment, as shown in FIG. 2, the eight-level system includes the middle modules, each of 125 cm in length and 100 cm in width.

Figure 4:
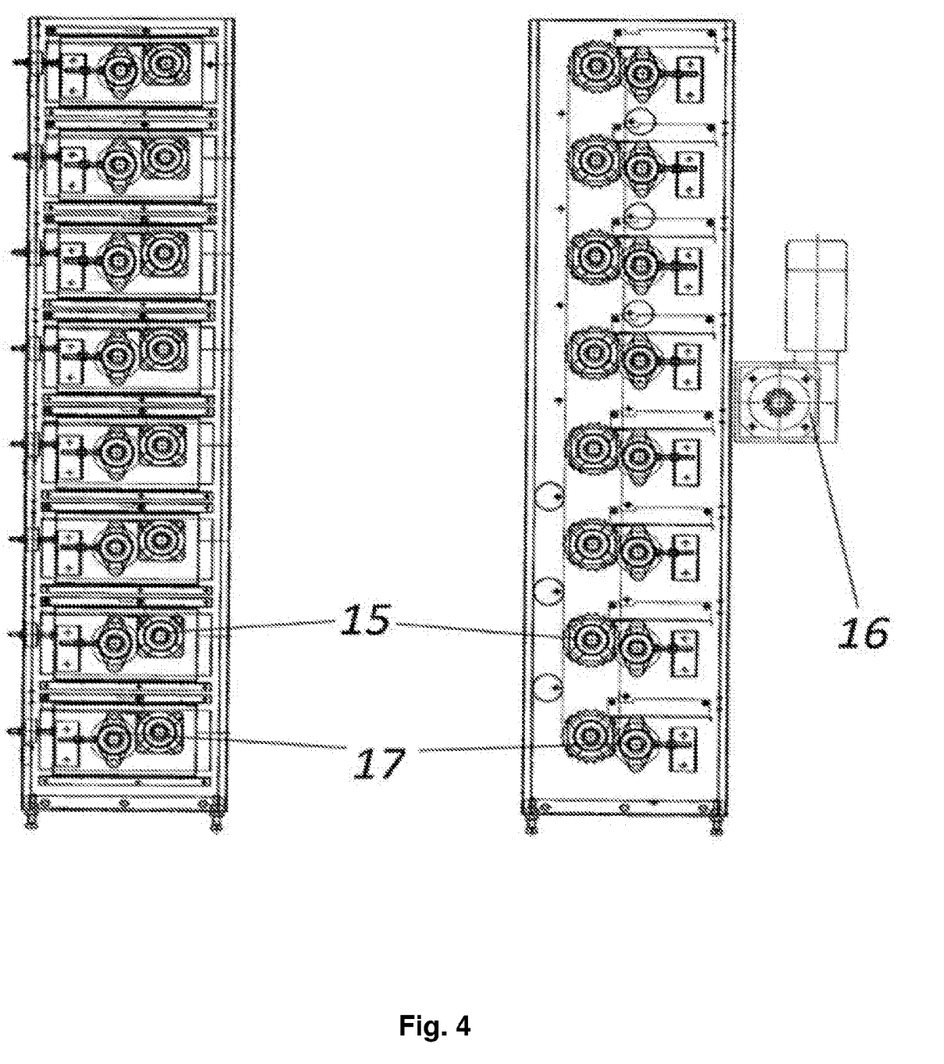
FIG. 4 shows side views, from both sides, for a front module of a technological line with a visible drive system.
Figure 5:
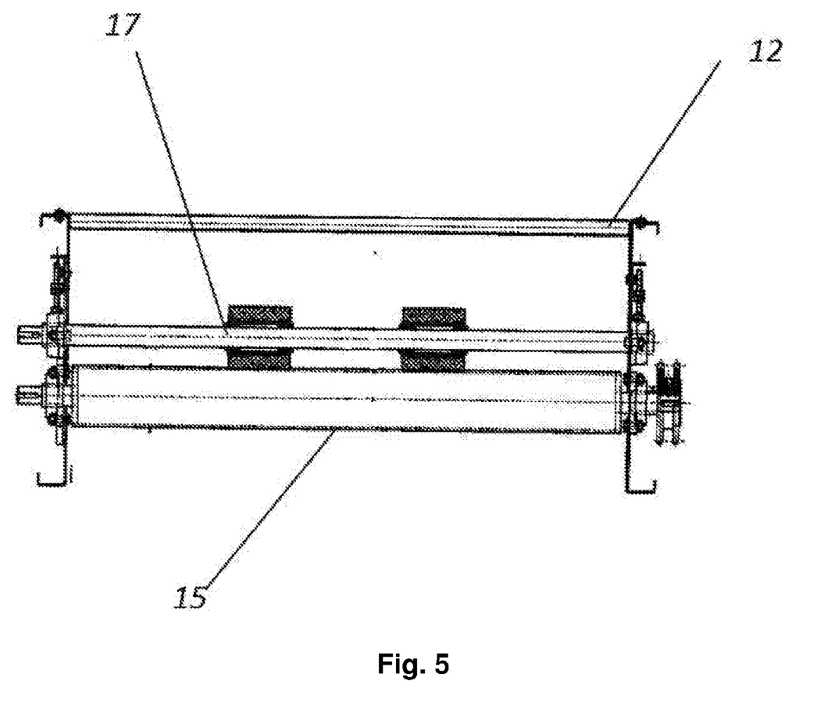
FIG. 5 shows a rear view of one level of a front module with a visible drive shaft 15 and a pressure roller 17.

The rear module 3 and the front module 4 are equipped with a tension system 8, and a driving shaft 15 and a pressure roller 17 respectively, allowing movement of the belt of the conveyor 11 made of plastic PVC using a drive system 16. The drive system 16 can be based on the usage of a geared motor or a crank drive. The drive system 16 allows synchronous startup of the drive of the conveyor belts of all levels by coupling them with conveyor belts. An exemplary drive system 16 is shown in FIG. 4 and FIG. 5.

In the present embodiment the technological line 1 is shown with eight levels 2, included within a system involving six middle modules 5a, 5b, 5c, 5d, 5e, 5f, however according to the invention the technological line can involve a different number of levels and the system, in accordance with the invention, can involve a different number of middle modules.

In the embodiment the system of the technological lines 1 with eight levels 2, shown in side view in FIG. 2, is made from galvanized steel sections with a thickness of 1.5 mm. The technological line for rearing/breeding insects, in the embodiment, is assembled from modules, including the rear module 3, six middle modules 5a, 5b, 5c, 5d, 5e, 5f and the front module 4. Each level in the rear module 3 is equipped with a movable ratchet rear end sidewall 9 with a spring clamp, a tension system 8 made up of a loose roller with a tension system, 60 mm in diameter, based on a turnbuckle, used to maintain and control the belt tension of the conveyor 11. The middle modules (5a, 5b, 5c, 5d, 5e, 5f) 1245 mm in length are equipped with legs 13 made of a steel profile, the profiled lateral sidewalls 6, 6b 100 mm in height, the inner edge thereof supporting the upper surface of the belt of the conveyor 11. The upper surface of the belt of the conveyor 11 is supported from below with the transverse brackets 12 (L profile) anchored in the profiled lateral sidewalls 6a, 6b, 20 mm in width, connecting the opposite profiled lateral sidewalls 6a, 6b. The transverse brackets 12 are located at intervals of 249 mm. The opposite legs 13 are connected with brackets 14 (C profile) with holes 50 mm in diameter, allowing installation of two optional feed supplying systems along the line. In the embodiment the height of a single level 2 is 25 cm.

Each level 2 in the front module 4 is equipped with a movable ratchet front end sidewall 10 with a spring clamp and a stiff rubber-coated drive shaft 15 with a rack and the axis allowing rotation of the shaft and movement of the belt of the conveyor 11 after releasing clamps of the end sidewalls 9 and 10. Preferably each drive shaft is linked with a central drive system 16 allowing synchronous movement of all or selected belts of the conveyor 11.

Each level 2 is equipped with a belt of the conveyor 11, the edges of the upper surface thereof resting on the profiled lateral sidewalls 6a, 6b, supported from below by the transverse brackets 12. The belt of the conveyor 11 covers the end shaft of the tension system 8 and the front drive shaft 15, which provide it with the appropriate tension. Under the influence of the load of the mass of the feed, the insects and the excrements cumulating on the surface of the belt of the conveyor 11, the edges of the belt of the conveyor 11 are pressed down against the profiled lateral sidewalls 6a, 6b, which provides sealing of the breeding line and prevents uncontrolled escape of the flightless insects and/or larvae of insects.

The steel profiled lateral sidewalls 6a, 6b have smooth surface, which does not allow the insects to climb.

The belt of the conveyor 11, made of polyvinylchloride (PVC), is welded and bonded to form a sleeve allowing fitting it on the drive mechanism and its movement. In the embodiment the usable area of a single level 2 is 8 m².

Example 2: Rearing of Mealworm Larvae (*Tenebrio molitor*)

The technological line according to Example 1 was used, with eight levels with the usable area of 8 m², with the belt of the conveyor 11 made of PVC. The experiments were carried out at a temperature of 28° C. and 50% humidity. The larvae were fed ad libitum with fruit and vegetable pulp concentrated with wheat bran to 35% water content.

The tests were carried out, which were intended to determine the maximum value range for the density of the larvae per unit area. To carry out the test five-week larvae of mealworm, 12-15 mm long, were chosen. The tests were carried out for a period of 3 days.

The transport boxes of e-2 type, made of high-density polyethylene (HDPE), commonly used for insect larvae rearing, were used as a control system. The control containers were located in the same room, in which the breeding line was placed.

During the period of 3 days the following was monitored: mobility of the insects, feeding, the maximum temperature the insects reached, consistency of the excrements cumulating on the surface of the belt. The incidence of mortality and insects distribution within the level (the belt) were also monitored.

TABLE 1

Influence of the number of insects per unit area on breeding parameters - the belt system.

| Number of insects per unit area | Distribution | Activity | Maximum registered temperature | Mortalities | Moisture content of excrements layer |
|---|---|---|---|---|---|
| 10 kg/m² | balanced | normal/feeding | 41.2° C. | none | dry, bulk |
| 15 kg/m² | balanced | normal/feeding | 41.3° C. | none | dry, bulk |
| 20 kg/m² | peripheral | normal/feeding | 42.1° C. | <1% | dry, bulk |

TABLE 2

Influence of the number of insects per unit area on breeding parameters - E-2 boxes.

| Number of insects per unit area | Distribution | Activity | Maximum registered temperature | Mortalities | Moisture content of excrements layer |
|---|---|---|---|---|---|
| 5 kg/m² | balanced | normal/feeding | 42.2° C. | none | dry, bulk |
| 10 kg/m² | peripheral | diminished/lack of feeding | 44.3° C. | 15-20% | agglomerated, moist |
| 15 kg/m² | peripheral | high mortality, poisoned individual insects/complete lack of feeding | 46.2° C. | >50% | wet |

Based on the tests it has been show that the technological line developed by the present inventors allows safe rearing of the mealworm larvae, while keeping the insects density at the level of 15 kg/m², without adverse impact on the breeding parameters. No symptoms of insects mortality or adverse effects, for example in the form of the insect aggregation in the vicinity of the sidewalls (peripheral distribution), testifying to overheating of the insects, have been observed.

The insect density over 10 kg/m² in the control containers, which are standard in rearing of the mealworm larvae, weakens the insects and leads to their death due to poor ventilation and overheating of the content of the breeding container.

The technological line according to the invention allows multiplying the insect breeding efficiency even four-fold.

Example 3: Rearing of *Hermetia* Larvae (*Hermetia illucens*)

The technological line according to Example 1 was used, with eight levels with the usable area of 8 m², with the belt of the conveyor made of PVC. The rearing was carried out at a temperature of 28° C. and 50% humidity. The larvae were fed ad libitum with fruit and vegetable pulp concentrated with wheat bran to 35% water content.

The rearing of the insects was done within the period of 14 days, starting from the larval stage L2/L3 to stage L5. The larvae L2/L3 were used, previously stored in an incubator for 7 days on a standard medium enriched with the addition of 10% yeasts, at a number of 60 or 90 thousand per square meter of the surface of the belt of the conveyor. During the rearing the following were controlled: mobility of the insects, feeding, consistency of the excrements cumulating on the surface of the belt. The incidence of mortalities and insects distribution within the level (the belt) were also observed.

Using the solution according to the invention allows intensive rearing of the *Hermetia illucens* larvae and minimizing the breeding risk in case when the number of larvae is between 50-80 thousand per square meter. During the rearing the distribution of insects was balanced (uniform), no insect aggregation in the vicinity of the belt sidewalls of the conveyor was observed, which indicates that the excess metabolic heat is efficiently dissipated from the breeding container. No escape of the larvae from the belt of the conveyor was observed. No death of the larvae was observed. At the end of this experiment the total weight of the larvae was measured after separation from the substrate, then the number of larvae was determined.

The measured values of insect growth from different groups were processed statistically according to SAS Institute standards. 1994. SAS User's Guide: Statistics. SAS Institute, Cary, N.C., USA. The results are presented in the table 3. Table 3 presents average values of the groups. BWG (Body Weight Gain); FI (Food Intake); FCR (Food Conversion Ratio).

TABLE 3

The results of rearing; the experiment on hermetia growth (n = 3).
Table 3 presents average values for the groups.

| Start number of larvae/8 m² | Final number of larvae | Final weight of larvae | BWG [kg] | FI [kg] | FCR |
|---|---|---|---|---|---|
| 480 000 | 437 000 | 89.15 kg | 88.15 | 416.95 | 4.73 |
| 720 000 | 656 000 | 135.14 kg | 133.64 | 640.14 | 4.79 |

The experiment has shown that the system developed by the present inventors allows safe rearing of the larvae of *hermetia* while maintaining a high level of bio-assurance. When the eight-level system is applied, the efficiency allows achieving 270 kg of fresh larvae weight per square meter of the breeding installation.

CONCLUSIONS

The initial experiments (Example 2 and 3) have shown functionality and efficiency of the technological line, according to the invention, in rearing of larvae of mealworm and *hermetia* using feed with high water content. It has been shown that the profiled lateral sidewalls made of steel together with the system of the horizontal reinforcements effectively dissipate excess heat, protecting the insects against overheating. At the same time example 2 has shown that the potential efficiency of the system significantly goes beyond the efficiency recognized for the systems existing on the market.

LIST OF INDICATIONS 1 technological line
2 level
3 rear module
4 front module
5a, 5b, 5c, 5d, 5e, 5f middle modules
6a, 6b profiled lateral sidewalls
7 spaces between levels
8 tension system
9 rear end sidewall
10 front end sidewall
11 conveyor belt
12 transverse bracket
13 leg
14 bracket
15 drive shaft
16 drive system
17 pressure roller
h—height of profiled lateral sidewall

The invention claimed is:

1. A technological line for rearing and/or breeding of flightless insects and/or larval forms of insects using feed in liquid or semi-liquid form, the technological line having at least one level, the technological line comprising:
an autonomous conveyor belt system defining a level of the at least one levels, the conveyor belt system comprising;
a plurality of transverse brackets extending generally horizontally;
two profiled lateral sidewalls spaced apart and interconnected by the transverse brackets, the sidewalls defining sides of the belt system along a direction of movement, the lateral sidewalls each having a generally vertical portion extending perpendicularly upwardly from the transverse brackets to an upper edge, the profiled lateral sidewalls having smooth surfaces, which do not allow the insects to climb; and
a movable belt having opposed longitudinal edges and an upper surface extending between the longitudinal edges, the movable belt being movable in the direction of movement, the movable belt having a belt width defined as a distance between the opposed longitudinal edges, the vertical portions of the lateral sidewalls being spaced apart by a distance less than the movable belt width;
the movable belt being disposed on and supported by the transverse brackets with the longitudinal edges of the movable belt curving up and extending up and being supported by the vertical portions of the lateral sidewalls such that the upper surface of the movable belt is curved upwardly at the longitudinal edges and the upper surface forms a trough profile;
upper edges of the profiled lateral sidewalls each extending inwardly toward the other lateral sidewall, a first bending angle (α) being an inside angle defined between each vertical portion and the respective upper edge of each profiled lateral sidewall, the first bending angle being not less than 30°, the upper edges of the lateral sidewalls extending inwardly over the longitudinal edges of the movable belt;
the movable belt and profiled lateral side walls configured such that a pressure of a mass of a working load of the liquid or semi-liquid feed and the insects disposed on the trough-profiled upper surface of the conveyor belt presses the longitudinal edges of the conveyor belt against the profiled lateral sidewalls to form self-sealing sidewalls;
corner spaces being defined between the conveyor belt and corners where the transverse brackets meet the profiled lateral sidewalls, the corner spaces allowing the self-sealing sidewalls to adjust a seal under the pressure of the mass of the working load;
wherein both the transverse brackets and the profiled lateral sidewalls are made of a material with efficient heat conducting properties, the material selected from metal or steel or stainless steel or galvanized steel; and
automatic feeders for supplying the liquid or semi-liquid feed.

2. The technological line according to claim 1, wherein:
the upper edge of each of the lateral sidewalls further has an inward portion bending downwardly toward the upper surface of the conveyor belt, a second inside bending angle being defined between the inward portion and a remainder of the respective upper edge, the second inside bending angle being in the range of 30° to 120°; and
the first bending angle being in the range of 30° to 120°.

3. The technological line according to claim 1, wherein a height of the profiled lateral sidewalls is not less than twice a maximum length of the insects.

4. The technological line according to claim 1, wherein the conveyor belt system further comprises legs and additional brackets extending between and connecting the legs, the brackets having at least one opening for installation of automatic feeders.

5. The technological line according to claim 1, wherein the at least one level comprises a plurality of levels, each level having a conveyor belt system, each of the conveyor belt systems being from 2 to 110 m long and from 0.5 to 3 m wide.

6. The technological line according to claim 1, wherein the conveyor belt is made of plastic, polyvinyl chloride (PVC), polypropylene (PP), or polystyrene (PS).

7. The technological line according to claim 1, wherein the technological line comprises a plurality of levels, spaces between the levels being maintained with a height being equal or greater than a height of the profiled lateral sidewalls.

8. The technological line according to claim 1, wherein the technological line comprises a mobile structure.

9. The technological line according to claim 1, wherein the first bending angle ($\alpha$) of the upper edge of each sidewall is 90° and the second bending angle between the inward portion and the remainder of the respective upper edge is 90°.

10. The technological line according to claim 1, wherein a water content in the liquid or semi-liquid feed is in the range of 15-45%.

11. The technological line according to claim 1, wherein the automatic system for supplying liquid or semi-liquid feed is a multi-point automatic system for supplying feed.

12. A modular system of technological lines for rearing and/or breeding of flightless insects and/or larval forms of insects, comprising:
    unified middle modules including technological lines according to claim 1; and
    a rear module with a rear end sidewall and a front module with a front end sidewall.

13. The modular system according to claim 12, wherein the rear end and front end sidewalls are movable.

14. The modular system according to claim 12, wherein the rear and front modules are equipped with tension systems, and drive shafts and pressure rollers respectively, allowing movement of the belt of the conveyor system using a mechanical or a manual drive.

15. A method of rearing and/or breeding of flightless insects and/or larval forms of insects using the feed in liquid or semi-liquid form, comprising a step of rearing and/or breeding of flightless insects and/or larval forms of insects using the technological line according to claim 1.

16. The method according to claim 15, wherein the insects are a larval form of insects and are the larvae of mealworm beetles and/or the larvae of hermetia illucens.

17. The method according to claim 16, wherein the larvae are fed with fruit and vegetable pulp and grain mill products.

18. The method according to claim 16, further comprising the step of feeding the larvae with the liquid or semi-liquid feed having a water content of 15-45%.

19. The method according to claim 18, wherein the larvae are fed with feed subjected to pre-fermentation.

20. A technological line for rearing and/or breeding of flightless insects and/or larval forms of insects using feed in liquid or semi-liquid form, the technological line having at least one level, the technological line comprising:
    an autonomous conveyor belt system defining a level of the at least one levels, the conveyor belt system comprising;
        a plurality of transverse brackets extending generally horizontally;
        two profiled lateral sidewalls spaced apart and interconnected by the transverse brackets, the sidewalls defining sides of the belt system along a direction of movement, the lateral sidewalls each having a generally vertical portion extending perpendicularly upwardly from the transverse brackets to an upper edge, the profiled lateral sidewalls having smooth surfaces, which do not allow the insects to climb; and
        a movable belt having opposed longitudinal edges and an upper surface extending between the longitudinal edges, the movable belt being movable in the direction of movement;
        the movable belt being disposed on and supported by the transverse brackets with the longitudinal edges of the movable belt curving up and extending up and being supported by the vertical portions of the lateral sidewalls such that the upper surface of the movable belt is curved upwardly at the longitudinal edges and the upper surface forms a trough profile;
        upper edges of the profiled lateral sidewalls each extending inwardly toward the other lateral sidewall, a first bending angle ($\alpha$) being an inside angle defined between each vertical portion and the respective upper edge of each profiled lateral sidewall, the first bending angle being not less than 30°, the upper edges of the lateral sidewalls extending inwardly over the longitudinal edges of the movable belt;
        the movable belt and profiled lateral side walls configured such that a pressure of a mass of a working load of the liquid or semi-liquid feed and including the insects disposed on the trough-profiled upper surface of the conveyor belt presses the longitudinal edges of the conveyor belt against the profiled lateral sidewalls to form self-sealing sidewalls;
        corner spaces being defined between the conveyor belt and corners where the transverse brackets meet the profiled lateral sidewalls, the corner spaces allowing the self- sealing sidewalls to adjust a seal under the pressure of the mass of the working load;
        wherein both the transverse brackets and the profiled lateral sidewalls are made of a material with efficient heat conducting properties, the material selected from metal or steel or stainless steel or galvanized steel; and
    automatic feeders for supplying the liquid or semi-liquid feed.

21. A technological line for rearing and/or breeding of flightless insects and/or larval forms of insects using feed in liquid or semi-liquid form, the technological line having at least one level, the technological line comprising:
    an autonomous conveyor belt system defining a level of the at least one levels, the conveyor belt system comprising;
        a plurality of transverse brackets extending generally horizontally;
        two profiled lateral sidewalls spaced apart and interconnected by the transverse brackets, the sidewalls defining sides of the belt system along a direction of movement, the lateral sidewalls each having a generally vertical portion extending perpendicularly upwardly from the transverse brackets to an upper edge, the profiled lateral sidewalls having smooth surfaces, which do not allow the insects to climb; and
        a movable belt having opposed longitudinal edges and an upper surface extending between the longitudinal edges, the movable belt being movable in the direction of movement;
        the movable belt being disposed on and supported by the transverse brackets with the longitudinal edges of the movable belt curving up and extending up and being supported by the vertical portions of the lateral sidewalls such that the upper surface of the movable belt is curved upwardly at the longitudinal edges and the upper surface forms a trough profile;

upper edges of the profiled lateral sidewalls each extending inwardly toward the other lateral sidewall, a first bending angle (α) being an inside angle defined between each vertical portion and the respective upper edge of each profiled lateral sidewall, the first bending angle being not less than 30°, the upper edges of the lateral sidewalls extending inwardly over the longitudinal edges of the movable belt;

the upper edge of each of the lateral sidewalls further having an inward portion bending downwardly toward the upper surface of the conveyor belt, a second inside bending angle being defined between the inward portion and a remainder of the respective upper edge, the second inside bending angle being in the range of 30° to 120°;

the movable belt and profiled lateral side walls configured such that a pressure of a mass of a working load of the liquid or semi-liquid feed and including the insects disposed on the trough-profiled upper surface of the conveyor belt presses the longitudinal edges of the conveyor belt against the profiled lateral sidewalls to form self-sealing sidewalls;

corner spaces being defined between the conveyor belt and corners where the transverse brackets meet the profiled lateral sidewalls, the corner spaces allowing the self- sealing sidewalls to adjust a seal under the pressure of the mass of the working load;

wherein both the transverse brackets and the profiled lateral sidewalls are made of a material with efficient heat conducting properties, the material selected from metal or steel or stainless steel or galvanized steel; and automatic feeders for supplying the liquid or semi-liquid feed.

* * * * *